US010265076B2

(12) United States Patent
Block

(10) Patent No.: US 10,265,076 B2
(45) Date of Patent: Apr. 23, 2019

(54) VASCULAR OCCLUDING BRIDGED SELF-EXPANDING METAL STENT (VOBSEMS)

(71) Applicant: Steven Clark Block, Lubbock, TX (US)

(72) Inventor: Steven Clark Block, Lubbock, TX (US)

(*) Notice: Subject to any disclaimer, the term of this patent is extended or adjusted under 35 U.S.C. 154(b) by 0 days.

(21) Appl. No.: 14/545,008

(22) Filed: Mar. 16, 2015

(65) Prior Publication Data
US 2016/0270794 A1    Sep. 22, 2016

(51) Int. Cl.
*A61B 17/12* (2006.01)
*A61F 2/82* (2013.01)
(Continued)

(52) U.S. Cl.
CPC .. *A61B 17/12177* (2013.01); *A61B 17/12031* (2013.01); *A61B 17/12109* (2013.01);
(Continued)

(58) Field of Classification Search
CPC .............. A61F 2/86; A61F 2002/016; A61B 17/12022; A61B 17/0057; A61B 2017/00526
See application file for complete search history.

(56) References Cited

U.S. PATENT DOCUMENTS 5,800,525 A * 9/1998 Bachinski ............... A61F 2/01
606/200
6,217,609 B1 * 4/2001 Haverkost ............... A61F 2/90
623/1.13
(Continued)

*Primary Examiner* — Julie A Szpira
(74) *Attorney, Agent, or Firm* — S&L US IP Attorneys, P.C.; Timothy Marc Shropshire; Eric Brandon Lovell

(57) ABSTRACT

This patent application is for the design of a vascular occluding bridged self-expanding metal stent (VOBSEMS) for fixed and immobile selective vascular occlusion and thrombosis of arteries and veins. Current vascular self-expanding metal stents (SEMS) are designed to open atherosclerotic arteries such as coronary arteries. Once deployed the SEMS remains immobile and permanent across the stenosis of the artery. In contradistinction to the SEMS which opens occluded stenotic arteries, the VOBSEMS is used to occlude and clot arterial and venous blood flow. The VOBSEMS clots blood vessels with unique metal bridges located inside the stent. The unique metal bridges are made of platinol a memory metal alloy identical to the stent, but imbedded with dacron fibers to promote clotting. The bridges are positioned inside of the VOBSEMS and secured to the stent by bridge end loop design. The bridges are staggered and rotated inside the stent with a spiral staircase appearance. The wire bridge is straight in the deployed or unsheathed position and acute angle in the undeployed or sheathed position. Therefore blood clots inside the VOBSEMS as blood flowing through a VOBSEMS encounters staggered and rotated intraluminal platinol bridges imbedded with thrombotic dacron fibers. Occlusion of arterial and venous blood flow can be used for inducing ischemia and congestion of tumors. Furthermore occlusion of arteries can be used as an angiographic adjunct to stopping hemorrhage from arteriovenous malformations, cerebral aneurysms and gastrointestinal bleeding.

15 Claims, 8 Drawing Sheets

Sequential rotated staggered intraluminal bridges of deployed VOBSEMS.

Dual channel VOBSEMS delivery system with one channel for stent and one channel for guidewire.

(51) Int. Cl.
  *A61F 2/90* (2013.01)
  *A61B 90/00* (2016.01)

(52) U.S. Cl.
  CPC .... *A61B 17/12172* (2013.01); *A61B 17/1214* (2013.01); *A61B 90/39* (2016.02); *A61B 2017/1205* (2013.01); *A61B 2090/3966* (2016.02); *A61F 2/82* (2013.01); *A61F 2/90* (2013.01)

(56) References Cited

U.S. PATENT DOCUMENTS

| | | | |
|---|---|---|---|
| 2002/0120276 A1* | 8/2002 | Greene, Jr. | A61B 17/12022 606/108 |
| 2005/0165480 A1* | 7/2005 | Jordan | A61B 17/12022 623/9 |
| 2006/0009798 A1* | 1/2006 | Callister | A61B 17/12022 606/200 |
| 2008/0147111 A1* | 6/2008 | Johnson | A61F 2/01 606/200 |
| 2014/0172074 A1* | 6/2014 | Concagh | A61F 2/90 623/1.19 |

* cited by examiner

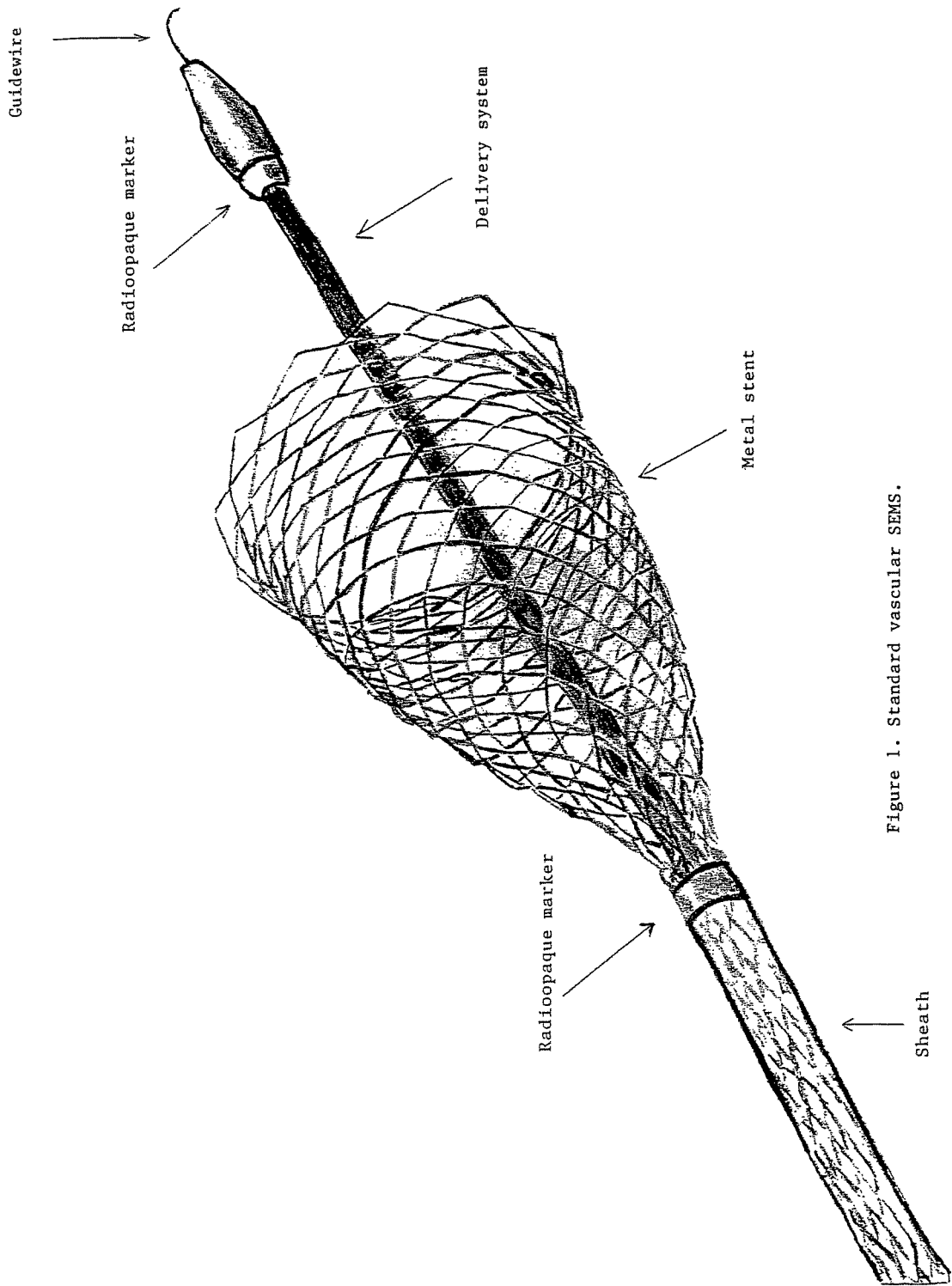
Figure 1. Standard vascular SEMS.

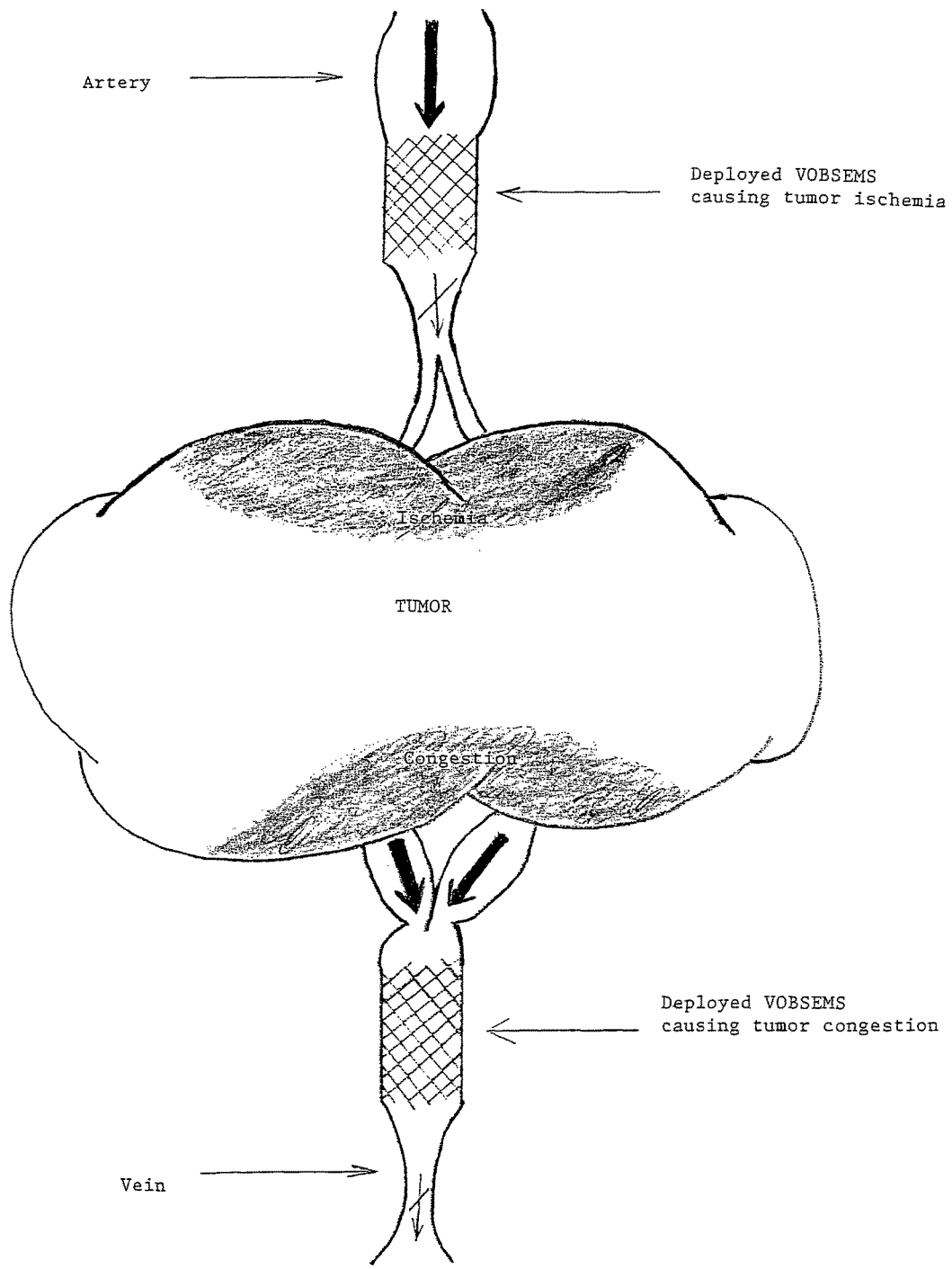
Figure 2. Deployed VOBSEMS occludes arterial inflow and venous outflow of tumor.

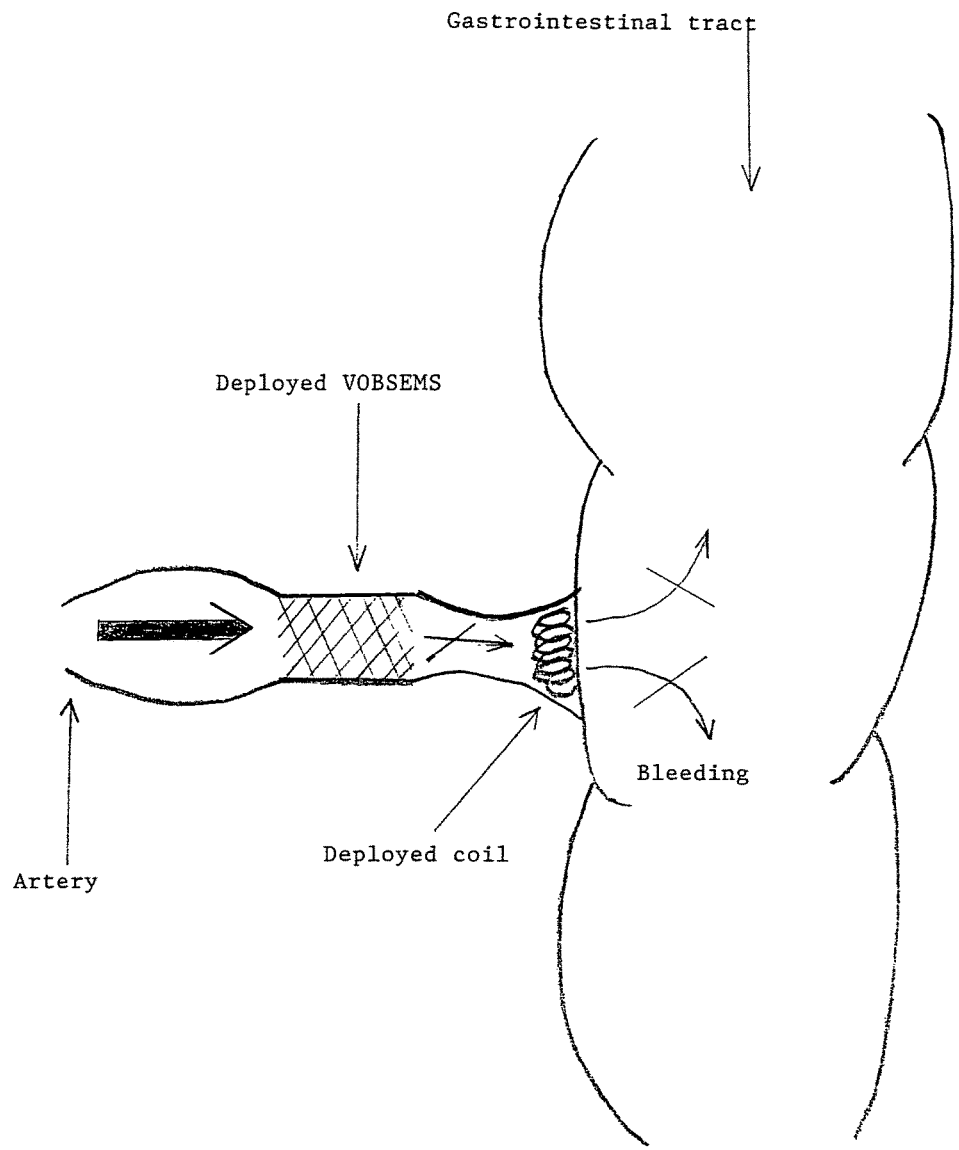
Figure 3. Deployed VOBSEMS used as adjunct to occlude persistently bleeding artery post coil embolization.

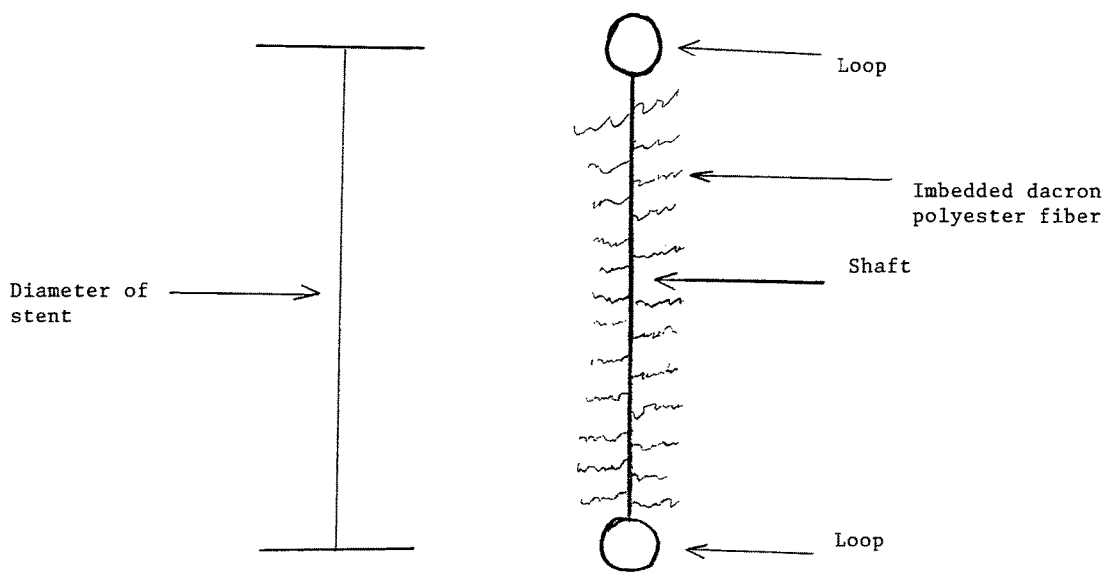
Figure 4. VOBSEMS intraluminal bridge in the unconstrained position. Shaft and loop of bridge made of memory platinol. Shaft imbedded with dacron polyester fiber to promote clotting. Distance between the center of the bridge loops is the diameter of the stent.

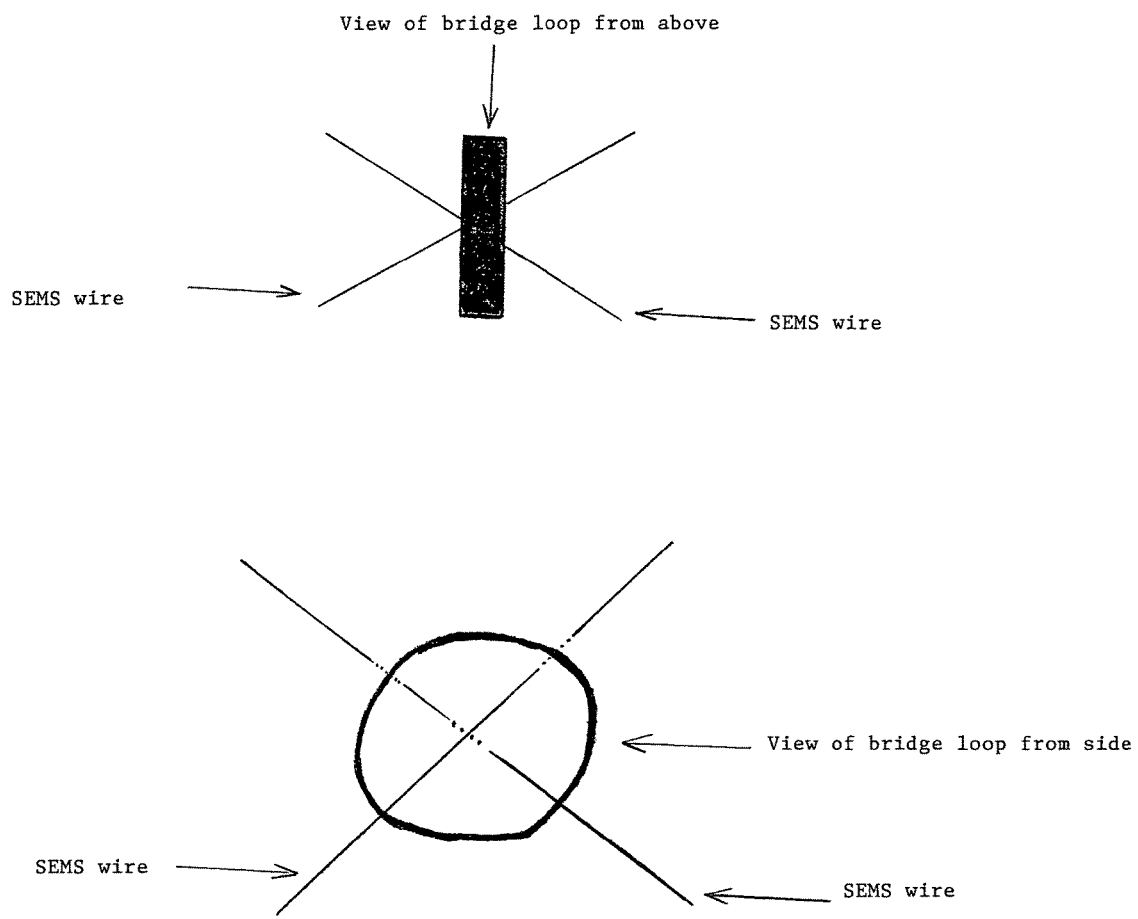
Figure 5. Positioning of SEMS wire mesh on bridge loop.

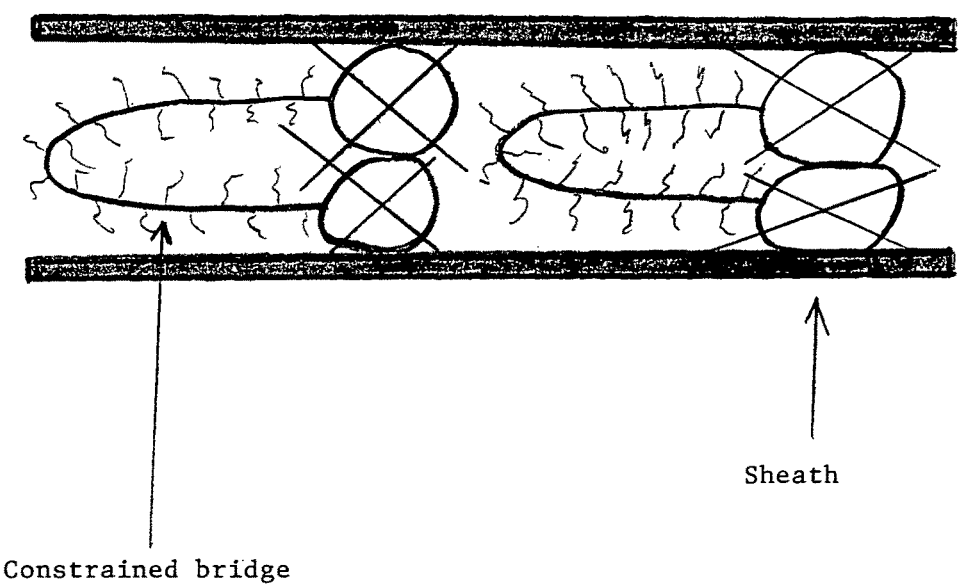
Figure 6. Staggered acute angle position of sequential constrained bridges of the VOBSEMS.

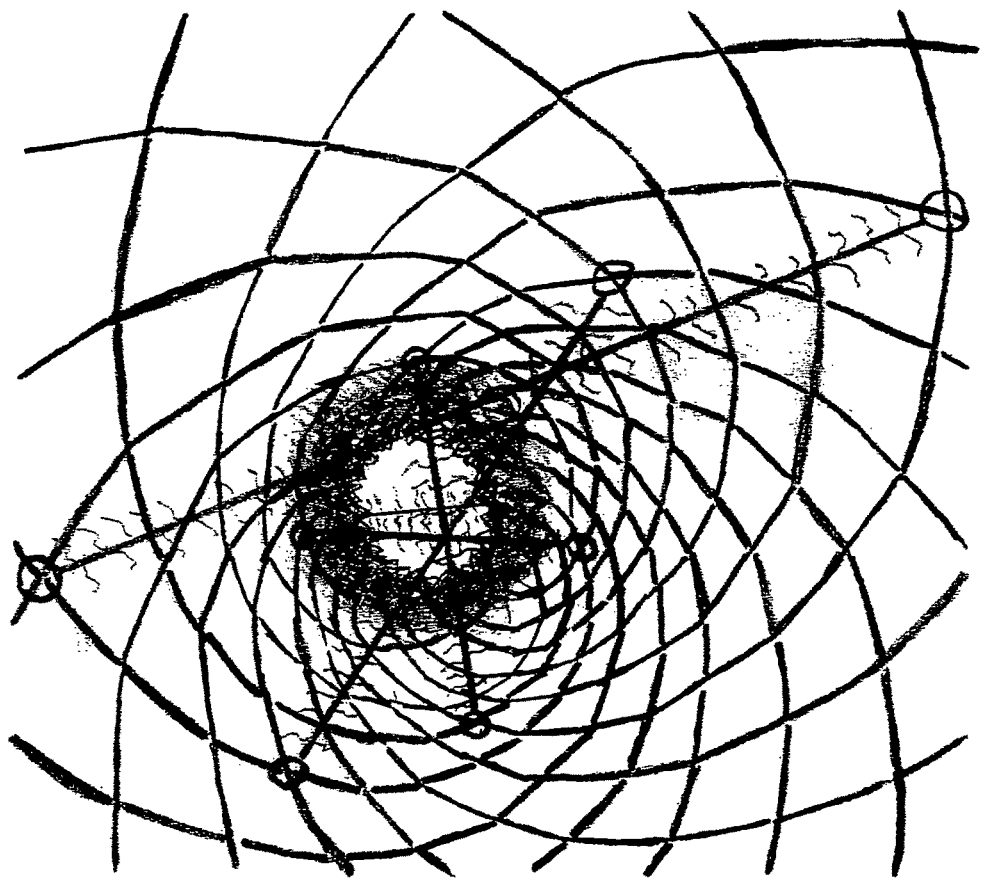
Figure 7. Sequential rotated staggered intraluminal bridges of deployed VOBSEMS.

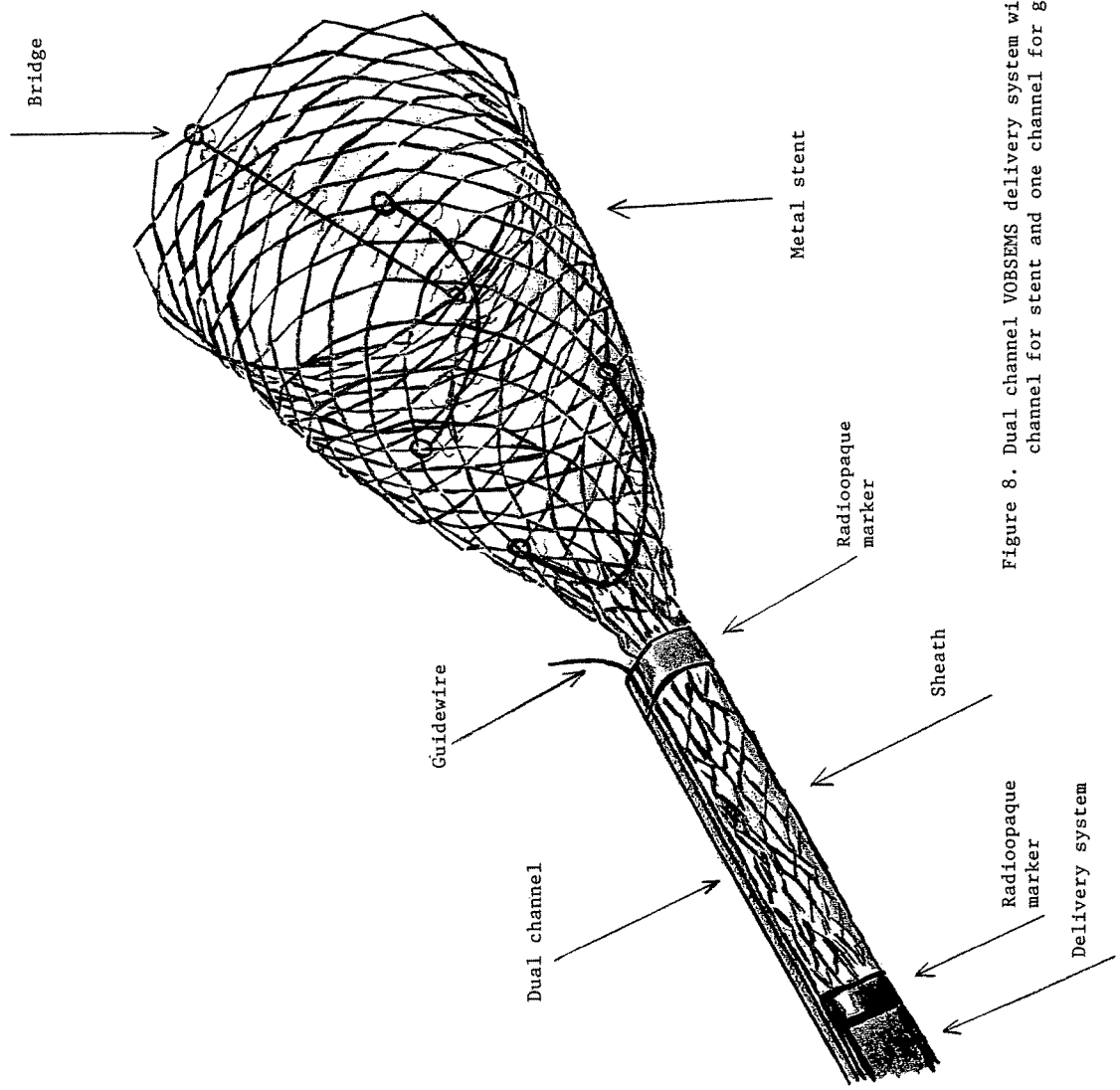
Figure 8. Dual channel VOBSEMS delivery system with one channel for stent and one channel for guidewire.

VASCULAR OCCLUDING BRIDGED SELF-EXPANDING METAL STENT (VOBSEMS)

Steven C. Block, M.D. makes this patent application for the design of a vascular occluding bridged self-expanding metal stent (VOBSEMS) for fixed and immobile selective vascular occlusion and thrombosis of arteries and veins. Current vascular self-expanding metal stents (SEMS) are designed to open atherosclerotic arteries such as coronary arteries. Once deployed the SEMS remains immobile and permanent across the stenosis of the artery. In contradistinction to the SEMS which opens occluded stenotic arteries, the VOBSEMS is used to occlude and clot arterial and venous blood flow. The VOBSEMS clots blood vessels with unique metal bridges located inside the stent. Occlusion of arterial and venous blood flow can be used for inducing ischemia and congestion of tumors. Furthermore occlusion of arteries can be used as an angiographic adjunct to stopping gastrointestinal bleeding.

Angiographic treatment of malignant tumor growth include transcatheter arterial chemoembolization (TACE) which is a minimally invasive procedure performed in interventional radiology to restrict a tumor's blood supply. Small embolic particles coated with chemotherapeutic agents are injected selectively in an artery supplying a tumor. TACE has most widely been applied to hepatocellular carcinoma for patients who are not eligible for surgery. TACE has been shown to increase survival in patients with intermediate hepatocellular carcinoma. Other treated malignancies include neuroendocrine tumors, ocular melanoma, cholangiocarcinoma, and sarcoma. TACE plays a palliative role in the more common metastatic colon carcinoma.

TACE is an interventional radiology procedure performed in the angiography suite. The procedure involves gaining percutaneous transarterial access to the hepatic artery with an arterial sheath, usually by puncturing the common femoral artery and passing a wire guided catheter into a branch of the hepatic artery supplying the tumor and threading smaller, more selective catheters into these branches. This is done to maximize the amount of chemotherapeutic dose that is directed to the tumor and minimize the amount of the chemotherapeutic agent that could damage the normal liver tissue. When a blood vessel supplying the tumor has been selected, alternating aliquots of the chemotherapy dose and of embolic particles, or particles containing the chemotherapy agent, are injected through the catheter. The total chemotherapeutic dose may be given in one vessel's distribution, or it may be divided among several vessels supplying the tumors.

TACE derives its beneficial effect by two primary mechanisms. The proper hepatic artery supplies most tumors within the liver; so arterial embolization preferentially interrupts the tumor's blood supply and stalls growth until neovascularization. Secondly, focused administration of chemotherapy allows for delivery of a higher dose to the tissue while simultaneously reducing systemic exposure, which is typically the dose-limiting factor. However, TACE only induces tumor necrosis in approximately 50% of patients; the resulting necrosis releases cytokines and other inflammatory mediators into the bloodstream. Therefore a self-limiting postembolization syndrome of pain, fever, and malaise may occur due to hepatocyte and tumor necrosis.

Other forms of angiographic treatment of malignant tumor growth include selective internal radiation therapy (SIRT), which is a form of radiation therapy used in interventional radiology to treat cancer. SIRT is used for selected patients with unresectable cancers that cannot be treated surgically such as hepatic cell carcinoma or metastasis to the liver. The treatment involves injecting tiny microspheres of radioactive material in the arteries that supply the tumor. During mesenteric angiography, once the branch of the hepatic artery supplying the tumor is identified and the tip of the catheter is selectively placed within the artery, yttrium-90 microspheres are infused.

Furthermore, the liver has a dual blood supply, receiving blood from the hepatic artery and the portal vein. Hepatic malignancies derive most of their blood supply from the hepatic artery; whereas the normal liver derives most of its blood supply from the portal vein. Therefore delivery of radioembolic particles through the branch of the hepatic artery supplying a tumor will preferentially lead to deposition of the particles in the tumor, while sparing normal liver from harmful side effects. However, complications of SIRT include postradioembolization syndrome (PRS), hepatic dysfunction, biliary complications, portal hypertension, radiation pneumonitis, gastrointestinal ulcers, vascular injury and lymphopenia. PRS include fatigue, nausea, vomiting, anorexia, fever, abdominal discomfort and cachexia, occurring in 20-55% of patients.

Also angiographic embolization is often used to treat hemorrhage with selective occlusion of blood vessels by introducing emboli and subsequently blocking a blood vessel. Angiographic embolization is used to treat a wide variety of bleeding conditions, such as arteriovenous malformations, cerebral aneurysm and gastrointestinal bleeding. Angiography is an endovascular procedure where access to the bleeding site is acquired by means of a guidewire and selective catheter. The position of the correct artery supplying the bleeding site in question is located by digital subtraction angiography. These images are then used as a map for the radiologist to gain access to the correct vessel by selecting an appropriate catheter and or wire. Once in place the artificial emboli can be introduced into the artery to flow passively downstream and subsequently lodge in a distal artery causing occlusion of the smaller artery. Mechanical occlusive devices such as coils are very good for fast-flowing vessels because of the immediate clot of the vessel. Coils are made from platinum or stainless steel and induce clot due to dacron polyester fibers imbedded in the wire of the coil.

Angiographic embolization of bleeding sites along with TACE and SIRT, require blood flow to lodge the embolic device down stream in the smaller blood vessel. Emboli that are either coated with chemotherapeutic agents or microspheres of radioactive material or metal coils imbedded with dacron polyester fibers are released angiographically and then flow downstream in order to occlude and embolize a blood vessel. However, passive flow embolization is limited to vessels such as arteries that flow toward the tumor or bleeding site. This type of embolization cannot occlude venous drainage flowing away from a vascular tumor. Furthermore, if gastrointestinal bleeding continues after embolization with a mechanical occlusive device further treatment of the persistently bleeding artery is limited.

Vascular self-expanding metal stents (SEMS) (FIG. 1) on the other hand have been used for fixed vascular placement and once self-expanded in the blood vessel are immobile. Vascular SEMS are commonly placed across a stenotic artery so that when unsheathed and deployed the area of narrowing of the artery is expanded to the larger diameter of the stent in order to improve blood flow across the stent. SEMS are cylindrical in shape, and are devised in a number of diameters and lengths to suit the size of the vessel being treated. SEMS typically consist of cross-hatched, braided or interconnecting rows of metal that are assembled into a tube-like structure. SEMS, when unexpanded, are small enough to fit into blood vessels as small as two millimeters in diameter. They expand through a deployment device, which is placed at the end of the SEMS. SEMS are made with platinol wire construction, which has a platinum core and nitinol encasement. Nitinol is shape memory nickel-titanium alloy, so that when the SEMS is unsheathed the memory metal will easily expand to its original shape.

The deployment device has two components, the stent and the stent delivery system. The delivery system consists of two coaxially arranged shafts: an inner shaft made of stainless steel proximally and thermoplast distally and an outer sheath made of thermoplast. The central lumen within the inner shaft continues to the tip and accepts a standard guidewire. The vascular SEMS is pre-loaded on the stent carrier located on the distal segment of the inner shaft. Two radiopaque markers on the inner shaft and one radiopaque marker on the retractable outer sheath are used to facilitate stent placement. The distal end of the outer sheath covers the SEMS and is used to deploy the stent during the interventional procedure.

A vascular occluding bridged self-expanding metal stent (VOBSEMS) is the proposed device for this patent application. The VOBSEMS is designed for fixed and immobile selective vascular occlusion and thrombosis of both arteries and veins. VOBSEMS can be deployed and subsequently occlude any blood vessel that fits the diameter of the stent. Currently that stent diameter can be as small as two millimeters in diameter. The vascular supply of a malignant tumor consists of arterial blood flow to the tumor and venous blood flow away from the tumor (FIG. 2). Because the deployed VOBSEMS is permanently fixed and does not require passive arterial flow for eventual thrombosis, the VOBSEMS can be deployed in both the arterial and venous vascular supply of a tumor. Angiographic embolization of a tumor artery leads to ischemia of the tumor, but a VOBSEMS deployed in a tumor artery and vein will cause both tumor ischemia and congestion. Furthermore once the vascular supply of any tumor is angiographically established, a VOBSEMS can easily be deployed to occlude arterial inflow to the tumor and venous outflow from the tumor. Also using the smaller diameter occluding stent and angiographically placing the stent in close proximity to the tumor can preserve blood flow to healthy tissue around the tumor.

A VOBSEMS can also be used in therapeutic angiography that does not involve inducing tumor ischemia and congestion. Therapeutic angiography used to treat persistent gastrointestinal hemorrhage involves deploying mechanical occlusive devices such as coils to occlude downstream arterial blood flow. In the event the coils have been deployed and gastrointestinal hemorrhage persists as noted on post embolic angiography, a VOBSEMS can be deployed proximal to the persistent arterial bleeding site as an adjunct to stop the gastrointestinal hemorrhage (FIG. 3).

A VOBSEMS consists of a standard vascular SEMS made of memory metal alloy that can be easily constrained with a standard sheath. However the VOBSEMS differs from a standard vascular SEMS in that the VOBSEMS has intraluminal bridging designed to clot and occlude blood vessels, both arteries and veins. The bridge portion of the VOBSEMS is made of platinol wire construction with a platinum core and nitinol encasement. On each end of the bridge is loop construction and the shaft of the platinol wire is imbedded with dacron polyester fibers to promote clotting (FIG. 4). Both ends of the bridge has a loop, so that the SEMS metal wires are placed through the loops at crossing points of the stent (FIG. 5). The platinol bridge is positioned inside the lumen of the SEMS from one wall of the stent to the opposite wall of the stent. The platinol wire construction of the bridge is flexible with full-length radiopacity and radial force when unsheathed to enhance full deployment and immobility of the stent. The shape memory of the platinol bridge is remembered in the straightened position when the VOBSEMS is deployed. The wire bridge is straight in the deployed or unsheathed position and acute angle in the undeployed or sheathed position. Therefore the constrained VOBSEMS smallest diameter would be when the loops on both ends of the bridge were touching in the acute angle shape (FIG. 6). Furthermore, when deployed, the diameter of the VOBSEMS will be the same as a standard SEMS because the bridge is located inside the lumen of the stent. Therefore the diameter of the VOBSEMS is the same diameter as the standard vascular SEMS. Also, the length of the VOBSEMS is the same length as the standard vascular SEMS. Angiographic assessment determines the optimal stent size and vessel location, with the goal of occluding as much vascular flow to and from a tumor while preserving vascular surrounding blood flow and drainage of healthy tissue. Furthermore, angiographic assessment of treating persistent gastrointestinal hemorrhage would include close proximity to the bleeding site in an effort to preserve vascular surrounding blood flow to nonbleeding healthy tissue.

In constructing the VOBSEMS the bridges of the VOBSEMS are placed inside the SEMS lumen starting at the distal end of the stent and extending the length of the stent to the furthest proximal location. As an example the first bridge placed inside the stent would have the loops at the end of the bridge located in the twelve and six o'clock position placed at the most distal point in the stent. The bridges would subsequently be staggered in order to not overlap in the constrained position and therefore preserve the smallest constrained diameter obtainable. The second bridge as an example is placed staggered and rotated to the one and seven o'clock position. The third bridge is again placed staggered and rotated to the two and eight o'clock position. The fourth bridge is placed staggered and rotated to the three and nine o'clock position and so forth until the full length of the stent contains rotated staggered bridges. When viewing the completely bridged unconstrained VOBSEMS, the lumen of the stent containing rotated staggered bridges would resemble a spiral staircase (FIG. 7). Blood flow obstruction and clotting is therefore enhanced by having the full length of the stent bridged with rotating bridges that are imbedded with dacron polyester fibers.

The standard vascular SEMS consists of memory metal alloy and is constrained in a standard fashion with a sheath located on a delivery device. The vascular SEMS delivery device has a central lumen within the inner shaft that continues to the tip of the device and accepts a standard guidewire. A guidewire through the lumen in the middle of the stent delivery device is needed for positioning and deploying the vascular SEMS. Because the VOBSEMS is bridged and constrained to the diameter of the touching end bridge loops that have been constrained to the acute angle shape, no wire access is available through the middle of the constrained VOBSEMS. Therefore the VOBSEMS has a dual channel delivery system with the guidewire lumen adjacent to the lumen containing the VOBSEMS stent. With the dual channel of the VOBSEMS, one channel would be for a guidewire and the adjacent second channel would be for the constrained VOBSEMS that would be sheathed but not located on an inner shaft that conflicts with the bridges (FIG. 8). The deployment device would have two components, the stent and the stent delivery system. The delivery system consists of one shaft made of thermoplast located distal to the stent, which is located easily by a radiopaque marker. The outer sheath is also made of thermoplast. Two radiopaque markers on the retractable outer sheath located at the distal and proximal end of the stent are used to facilitate stent location and placement. The distal end of the outer sheath covers the VOBSEMS and is used to deploy the stent during the interventional procedure. Once guidewire location has been obtained and the VOBSEMS properly positioned in the target vessel, the guidewire would be withdrawn in to the lumen of the delivery system in order to not be trapped when deploying the VOBSEMS. Once exact location of the target vessel is verified, the VOBSEMS would be unsheathed and unconstrained to occlude the blood vessel. Furthermore, a unique advantage of the VOBSEMS is the stents immobility once deployed and therefore the stent does not require passive arterial blood flow for embolization as needed by current angiographic technique. The deployed VOBSEMS can therefore be permanently fixed in both artery and vein.

Tumor ischemia and congestion induced by occlusion of both arterial and venous blood flow offers additional treatment options for patients with metastatic malignancies or unresectable malignancies that are not amenable to chemo-radiation therapy. The VOBSEMS is an immobile occluding vascular stent that occludes blood flow to and from a tumor promoting necrosis and congestion of such malignancies. In addition, the smaller diameter VOBSEMS occludes vessels in close proximity to the tumor to further preserve the vascular supply and drainage of healthy surrounding tissue. Also, for the treatment of gastrointestinal hemorrhage, the VOBSEMS is an effective adjunct to occluding persistently bleeding arteries.

REFERENCES

1. Guan Y S, He Q, Wang M Q (2012). "Transcatheter arterial chemoembolization: history for more than 30 years". *ISRN Gastroenterol*.
2. Brown D B, Geschwind J F, Soulen M C, Millward S F, Sacks D (2006). "Society of Interventional Radiology position statement on chemoembolization of hepatic malignancies". *J Vasc Interv Radiol* 17 (2): 217-23. doi:10.1097/01.rvi.0000196277.76812.a3.
3. Miraglia R, Pietrosi G, Maruzzelli L, et al. (2007). "Efficacy of transcatheter embolization/chemoembolization (TAE/TACE) for the treatment of single hepatocellular carcinoma". *World J Gastroenterol* 13 (21): 2952-5.
4. Rammohan A, Sathyanesan J, Ramaswami S, et al. (2012). "Embolization of liver tumors: Past, present and future". *World J Radiol* 4 (9): 405-12. doi:10.4329/wjr.v4.i9.405.
5. Stuart K (2003). "Chemoembolization in the management of liver tumors". *Oncologist* 8 (5): 425-37. doi:10.1634/theoncologist.8-5-425.
6. http://www.plasmachem.com/dlc-mirco-f12-stent.html
7. http://www.bostonscientific.com/content/dam/bostonscientific/endo/portfolio-group/wallflex-rx-biliary-stents/wallflexbiliary_productinfo_brochure.pdf
8. Atassi, B; Gates V L; Lewandowski R J; et al (2007). "Radioembolization with Yttrium-90 microspheres: review of an emerging treatment for liver tumors". *Future Oncology* 3 (1).
9. Kennedy, A; Nag S; Salem R; et al (2007). "Recommendations for radioembolization of hepatic malignancies using yttrium-90 microsphere brachytherapy: a consensus panel report from the radioembolization brachytherapy oncology consortium". *Int J Radiat Oncol Biol Phys* 68 (1).
10. Salem, R; Lewandowski R J; Mulcahy M F; et al (2010). "Radioembolization for Hepatocellular Carcinoma Using Yttrium-90 Microspheres: A Comprehensive Report of Long-term Outcomes". *Gastroenterology* 138 (1).
11. Nicolay, N H; Berry D P; Sharma R A (2009). "Liver metastases from colorectal cancer: radioembolization with systemic therapy". *Nat Rev Clin Oncol* 6 (12).
12. Rhee, T K; Lewandowski R J; Liu D M; et al (2008). "90Y Radioembolization for metastatic neuroendocrine liver tumors: preliminary results from a multi-institutional experience". *Ann Surg* 247 (6).
13. http://clinicaltrials.gov/ct2/show/NCT01135056 Study to Compare Selective Internal Radiation Therapy (SIRT) Versus Sorafenib in Locally Advanced Hepatocellular Carcinoma (HCC)
14. Riaz, A; Lewandowski R J; Kulik L M; et al (2009). "Complications Following Radioembolization with Yttrium-90 Microspheres: A Comprehensive Literature Review". *Journal of Vascular and Interventional Radiology* 20 (9).
15. Chauleur C, Fanget C, Tourne G, Levy R, Larchez C, Seffert P; Fanget; Tourne; Levy; Larchez; Seffert (2008). "Serious primary post-partum hemorrhage, arterial embolization and future fertility: a retrospective study of 46 cases". *Hum. Reprod.* 23 (7): 1553-1559. doi:10.1093/humrep/den122. PMID 18460450.
16. Whittingham-Jones, P.; Baloch, I.; Miles, J.; Ferris, B (2010). "Persistent haemarthrosis following total knee arthroplasty caused by unrecognised arterial injury". *Grand Rounds* 10: 51-54. doi:10.1102/1470-5206.2010.0010 (inactive 2015-01-12).
17. Naji Alhamid1, Hani Alterkyl, Mohammad Imad Othman2 (2011-02-05). "Renal artery embolization for managing uncontrolled hypertension in a kidney transplant candidate Aihamid N, Alterky H, Othman M I". Avicenna J Med. doi:10.4103/2231-0770.112791. Retrieved 2014-01-09.
18. Gelfoam at Pfizer
19. Carretero, C; Munoz-Navas, M; Betes, M; Angos, R; Subtil, J C; Fernandez-Urien, I; De La Riva, S; Sola, J et al. (2007). "Gastroduodenal injury after radioembolization of hepatic tumors". *The American journal of gastroenterology* 102 (6): 1216-20. doi:10.1111/j.1572-0241.2007.01172.x. PMID 17355414.
20. Arepally, A; Chomas, J; Kraitchman, D; Hong, K (2013). "Quantification and reduction of reflux during embolotherapy using an antireflux catheter and tantalum microspheres: Ex vivo analysis". *Journal of vascular and interventional radiology: JVIR* 24 (4): 575-80. doi: 10.1016/j.jvir.2012.12.018. PMID 23462064.
21. http://www.birthmarks.us/embolization.htm
22. http://www.roneurosurgery.eu/atdoc/7ChiriacAIEmbolic.pdf
23. http://www.bostonscientific.com/en-US/products/stents—vascular/Carotid_WALLSTENT_Monorail_Endoprosthesis.html
24. Vitale G, Davis B, Tran T (2005). "The advancing art and science of endoscopy". *Am J Surg* 190 (2): 228-33. doi:10.1016/j.amjsurg.2005.05.017. PMID 16023436.
25. Mauro M, Koehler R, Baron T (2000). "Advances in gastrointestinal intervention: the treatment of gastroduodenal and colorectal obstructions with metallic stents". *Radiology* 215 (3): 659-69. doi:10.1148/radiology.215.3.r00jn30659. PMID 10831681.

26. Schmassmann A, Meyenberger C, Knuchel J, Binek J, Lammer F, Kleiner B, Hürlimann S, Inauen W, Hammer B, Scheurer U, Halter F (1997). "Self-expanding metal stents in malignant esophageal obstruction: a comparison between two stent types". *Am J Gastroenterol* 92 (3): 400-6. PMID 9068458.

27. Song H, Park S, Jung H, Kim S, Kim J, Huh S, Kim T, Kim Y, Park S, Yoon H, Sung K, Min Y (1997). "Benign and malignant esophageal strictures: treatment with a polyurethane-covered retrievable expandable metallic stent". *Radiology* 203 (3): 747-52. doi:10.1148/radiology.203.3.9169699. PMID 9169699.

28. Saxon R, Morrison K, Lakin P, Petersen B, Barton R, Katon R, Keller F (1997). "Malignant esophageal obstruction and esophagorespiratory fistula: palliation with a polyethylene-covered Z-stent". *Radiology* 202 (2): 349-54. doi:10.1148/radiology.202.2.9015055. PMID 9015055.

29. EII C, Hochberger J, May A, Fleig W, Hahn E (1994). "Coated and uncoated self-expanding metal stents for malignant stenosis in the upper GI tract: preliminary clinical experiences with Wallstents". *Am J Gastroenterol* 89 (9): 1496-500. PMID 7521573.

30. Decker P, Lippler J, Decker D, Hirner A (2001). "Use of the Polyflex stent in the palliative therapy of esophageal carcinoma: results in 14 cases and review of the literature". *Surg Endosc* 15 (12): 1444-7. doi:10.1007/s004640090099. PMID 11965462.

31. Nelson D, Silvis S, Ansel H (1994). "Management of a tracheoesophageal fistula with a silicone-covered self-expanding metal stent.". *Gastrointest Endosc* 40 (4): 497-9. doi:10.1016/S0016-5107(94)70221-7. PMID 7523233.

32. Holt A, Patel M, Ahmed M (2004). "Palliation of patients with malignant gastroduodenal obstruction with self-expanding metallic stents: the treatment of choice?". *Gastrointest Endosc* 60 (6): 1010-7. doi:10.1016/S0016-5107(04)02276-X. PMID 15605026.

33. Fiorini A, Fleischer D, Valero J, Israeli E, Wengrower D, Goldin E (2000). "Self-expandable metal coil stents in the treatment of benign esophageal strictures refractory to conventional therapy: a case series.". *Gastrointest Endosc* 52 (2): 259-62. doi:10.1067/mge.2000.107709. PMID 10922106.

34. Gelbmann C, Ratiu N, Rath H, Rogler G, Lock G, Scholmerich J, Kullmann F (2004). "Use of self-expandable plastic stents for the treatment of esophageal perforations and symptomatic anastomotic leaks.". *Endoscopy* 36 (8): 695-9. doi:10.1055/s-2004-825656. PMID 15280974.

35. Yoshida H, Mamada Y, Taniai N, Mizuguchi Y, Shimizu T, Aimoto T, Nakamura Y, Nomura T, Yokomuro S, Arima Y, Uchida E, Misawa H, Uchida E, Tajiri T (2006). "Fracture of an expandable metallic stent placed for biliary obstruction due to common bile duct carcinoma.". *J Nippon Med Sch* 73 (3): 164-8. doi:10.1272/jnms.73.164. PMID 16790985.

36. Kauffmann G, Roeren T, Friedl P, Brambs H, Richter G (1990). "Interventional radiological treatment of malignant biliary obstruction". *Eur J Surg Oncol* 16 (4): 397-403. PMID 2199224.

37. Cordero J, Moores D (2000). "Self-expanding esophageal metallic stents in the treatment of esophageal obstruction". *Am Surg* 66 (10): 956-8; discussion 958-9. PMID 11261624.

38. Ramirez F, Dennert B, Zierer S, Sanowski R (1997). "Esophageal self-expandable metallic stents—indications, practice, techniques, and complications: results of a national survey.". *Gastrointest Endosc* 45 (5): 360-4. doi:10.1016/S0016-5107(97)70144-5. PMID 9165315.

39. Schiefke I, Zabel-Langhennig A, Wiedmann M, Huster D, Witzigmann H, Mossner J, Berr F, Caca K (2003). "Self-expandable metallic stents for malignant duodenal obstruction caused by biliary tract cancer.". *Gastrointest Endosc* 58 (2): 213-9. doi:10.1067/mge.2003.362. PMID 12872088.

40. Yoon W, Lee J, Lee K, Lee W, Ryu J, Kim Y, Yoon Y (2006). "A comparison of covered and uncovered Wallstents for the management of distal malignant biliary obstruction". *Gastrointest Endosc* 63 (7): 996-1000. doi: 10.1016/j.gie.2005.11.054. PMID 16733115.

41. Garcia-Cano J, Gonzalez-Huix F, Juzgado D, Igea F, Perez-Miranda M, Lopez-Roses L, Rodriguez A, Gonzalez-Carro P, Yuguero L, Espinos J, Ducons J, Orive V, Rodriguez S. (2006). "Use of self-expanding metal stents to treat malignant colorectal obstruction in general endoscopic practice (with videos)". *Gastrointest Endosc* 64 (6): 914-920. doi:10.1016/j.gie.2006.06.034. PMID 17140898.

42. Vakil N, Morris A, Marcon N, Segalin A, Peracchia A, Bethge N, Zuccaro G, Bosco J, Jones W (2001). "A prospective, randomized, controlled trial of covered expandable metal stents in the palliation of malignant esophageal obstruction at the gastroesophageal junction.". *Am J Gastroenterol* 96 (6): 1791-6. doi:10.1111/j.1572-0241.2001.03923.x. PMID 11419831.

43. Conio M, Gostout C (1998). "Photodynamic therapy for the treatment of tumor ingrowth in expandable esophageal stents.". *Gastrointest Endosc* 48 (2): 225. doi:10.1016/S0016-5107(98)70175-0. PMID 9717799.

44. Matsushita M, Takakuwa H, Nishio A, Kido M, Shimeno N (2003). "Open-biopsy-forceps technique for endoscopic removal of distally migrated and impacted biliary metallic stents". *Gastrointest Endosc* 58 (6): 924-7. doi: 10.1016/S0016-5107(03)02335-6. PMID 14652567.

45. Grover S C, Wang C S, Jones M B, Elyas M E, Kortan P P. "Iatrogenic intussusception of a self-expanding metallic esophageal stent in stent after endoscopic guidewire trauma. Abstract presented at Canadian Association of Gastroenterology Meetings, February 2006". Retrieved 2006-12-07.

46. http://www.bostonscientific.com/content/dam/bostonscientific/pi/portfolio-group/eDFU/Carotid_WALLSTENT_dfu_90691219-01A_us.pdf

BRIEF DESCRIPTION OF DRAWINGS

FIG. 1 is a side profile of a standard vascular self-expanding metal stent (SEMS) partially deployed;

FIG. 2 is an illustration showing deployed vascular occluding self-expanding metal stents (VOBSEMS) occluding arterial inflow and venous outflow of a tumor;

FIG. 3 is an illustration showing a deployed VOBSEMS being used an adjunct to occlude a persistently bleeding artery after coil embolization;

FIG. 4 shows a VOBSEMS intraluminal bridge in the unconstrained position with the distance from the center of the bridge loops being the diameter of the unconstrained stent;

FIG. 5 illustrates the position of the SEMS wire mesh secured through the loops of the bridge, with views above and from the side of the bridge loop;

FIG. 6 shows a side profile of a constrained VOBSEMS illustrating the acute angle position of the staggered constrained bridges;

FIG. 7 illustrates the perspective view of looking through a deployed VOBSEMS with sequential rotated staggered intraluminal bridges resembling a spiral staircase;

FIG. 8 is a side profile of a VOBSEMS partially deployed.

I claim:

1. A clotting device comprising:
   a) a housing including:
      i) a first channel; and
      ii) a second channel positioned adjacent, and parallel, to the first channel;
   b) a guidewire removably positioned within the first channel;
   c) a stent removably positioned within the second channel;
   d) a sheath removably positioned around the housing; and
   e) a plurality of bridges positioned within the stent, wherein each bridge includes:
      i) a shaft;
      ii) a first loop positioned at a first end of the shaft;
      iii) a second loop positioned at a second end of the shaft; and
      iv) a plurality of fibers extending from the shaft,
      wherein the first loop and the second loop, respectively, are secured to opposing stent walls,
   wherein the bridges are longitudinally displaced from one another, such that each bridge occupies a unique longitudinal position along the length of the stent,
   wherein the bridges are rotationally staggered about an axis of the stent,
   wherein, in a constrained position, the bridges are bent from a native shape and are constrained by the sheath,
   wherein, when the sheath is removed, the bridges return to their native shape, causing the stent to deploy to an expanded position, wherein the clotting device is configured to clot and occlude arteries and veins.

2. The clotting device of claim 1, wherein the bridges are collectively arranged, such that, in the expanded position, they form a spiral staircase-like structure.

3. The clotting device of claim 1, wherein a first bridge is located at a distal end of the stent, and wherein a last bridge is located at a proximal end of the stent, wherein a remainder of the bridges are positioned between the first bridge and the last bridge.

4. The clotting device of claim 3, wherein the first loop of the first bridge is secured to a twelve o'clock position on a wall of the stent, and wherein the second loop of the first bridge is secured to a six o'clock position on the stent wall, wherein each successive bridge, up to and including the last bridge, is rotated about the stent axis a pre-determined degree of rotation, relative to a position of an immediately preceding bridge.

5. The clotting device of claim 1, wherein a first radio-opaque marker and a second radio-opaque marker are directly attached to the sheath, wherein the first radio-opaque marker is positioned within a distal portion of the sheath, and wherein the second radio-opaque marker is displaced from the first radio-opaque marker.

6. The clotting device of claim 1, wherein a diameter of the second channel is larger than a diameter of the first channel.

7. The clotting device of claim 1, wherein the fibers are dacron polyester fibers.

8. The clotting device of claim 1, wherein the stent is constructed of a memory metal alloy having a platinum core and a nitinol encasement.

9. The clotting device of claim 8, wherein the shaft is constructed of the memory metal alloy.

10. The clotting device of claim 1, wherein the sheath is constructed of a thermoplastic material.

11. The clotting device of claim 1, wherein, in the constrained position, the first loop and the second loop of each bridge, respectively, contact one another.

12. The clotting device of claim 11, wherein, in the constrained position, the shaft of each bridge is bent so as to form an acute angle.

13. The clotting device of claim 12, wherein, in the expanded position, the shaft of each bridge is straight.

14. A method of using the clotting device of claim 1, the method comprising the steps of:
   a) positioning the clotting device at a pre-determined location in a blood vessel;
   b) withdrawing the guidewire from the first channel and into the second channel; and
   c) removing the sheath from around the housing,
   wherein, upon removal of the sheath, the bridges return to their native shape, resulting in deployment of the stent,
   wherein, if the blood vessel is an artery, the pre-determined location is upstream of a tumor, and
   wherein, if the blood vessel is a vein, the pre-determined location is downstream of the tumor.

15. A method of using the clotting device of claim 1, the method comprising the steps of:
   a) positioning the clotting device at a pre-determined location in a blood vessel;
   b) withdrawing the guidewire from the first channel and into the second channel; and
   c) removing the sheath from around the housing,
   wherein, upon removal of the sheath, the bridges return to their native shape, resulting in deployment of the stent,
   wherein the pre-determined location is upstream of a coil of an angiographic embolization device.

* * * * *